United States Patent [19]
Johnson et al.

[11] Patent Number: 5,653,720
[45] Date of Patent: Aug. 5, 1997

[54] SURGICAL CLIP AND METHOD OF ASSEMBLY

[75] Inventors: Gary M. Johnson, Mission Viejo; Donald L. Gadberry, San Juan Capistrano, both of Calif.

[73] Assignee: Applied Medical Resources, Laguna Hills, Calif.

[21] Appl. No.: 504,122

[22] Filed: Jul. 18, 1995

[51] Int. Cl.$^6$ .................................................. A61B 17/08
[52] U.S. Cl. ............................................ 606/151; 606/158
[58] Field of Search ................................. 606/151, 157, 606/158, 120

[56] References Cited

U.S. PATENT DOCUMENTS 4,931,058  6/1990  Cooper ..................................... 606/158

Primary Examiner—Michael Buiz
Assistant Examiner—Kevin Troung
Attorney, Agent, or Firm—Richard L. Myers

[57] ABSTRACT

A parallel jaw clip comprises a barrel base and a barrel cap which when joined together forming an outer barrel, a hollow plunger which fits within the outer barrel, and a spring positioned within the hollow plunger. The outer barrel which permits the plunger to slidably move within the outer barrel and return to its original position, a clamping jaw on the barrel cap and the plunger which are parallel to each other and which face each other to grasp an object. Also disclosed is a method for assembling a parallel jaw clip comprising placing a spring within the barrel base, placing a plunger within the barrel base so that the spring is within the hollow interior of the plunger, placing the barrel cap over the plunger and the barrel base, attaching the barrel cap to the base, and positioning the plunger top so that it remains outside the aperture in the barrel cap.

24 Claims, 3 Drawing Sheets

SURGICAL CLIP AND METHOD OF ASSEMBLY

BACKGROUND OF THE INVENTION

The present invention relates to surgical clips of the type referred to as parallel jaw clips, and improved methods for assembling such clips.

In many surgical procedures, a considerable number of surgical clips are used to occlude severed blood vessels and other body conduits. A common type of clip is the parallel jaw clip which includes a pair of jaws at least one of which is moveable to open and close the jaws of the clip. Parallel jaw clips have a number of advantages over other types of surgical clips. Some of the advantages include easy and dependable placement on a blood vessel, reliable occlusion when so placed, and simple removal as the surgery is completed. Parallel jaw clips must be economical to manufacture so they can be discarded after use. This is because of the difficulty involved in sterilizing and reusing the clips.

Clips of the past have frequently failed to meet all of these design, cost, and performance criteria. Many clips have been designed and produced with component parts which must be adhesively bonded together. Use of adhesives having the necessary bonding strength and long-term durability usually requires a set time which adds to the production cost. Also, adhesive overflow or flow outside the joint to be bonded can require a clean-up step or the discarding of defective clips. It would be advantageous to have a surgical clip of the parallel jaw design which is economical to produce, dependable to use, and designed for easy application and removal from a blood vessel.

The prior art relating to parallel jaw surgical clips is represented by U.S. Pat. No. 4,931,058 issued to Cooper and entitled PARALLEL JAW SPRING CLIP AND METHOD OF MAKING SAME. This clip was designed in part to overcome the difficulty encountered in the manufacture of other clips using adhesively bonded joints. The design used snap fittings in combination with a resilient polymeric composition, which yields under pressure, to snap the component parts together. Because of the large width of the slots required, as well as the resilient properties of the polymeric composition used to make the component parts, such a design as the one shown in FIG. 1 of the Cooper patent has occasionally exhibited a "scissoring" effect where the jaws do not remain in alignment used to occlude a large blood vessel or other body conduit. The "scissoring" effect produces an incomplete occlusion of the object. Hence the level of development of parallel jaw clips continues to provide opportunities for further improvements in the design and manufacture of such surgical aids.

SUMMARY OF THE INVENTION

The present invention relates to a parallel jaw clip comprising an outer barrel interengaged with an inner plunger. Both the outer barrel and the inner plunger are hollow. In its broadest aspects, the present invention relates to a parallel jaw clip which has a spring positioned within the hollow interior of the barrel and the plunger. The barrel has a closed end upon which end the opposite end of the spring rests. The closed end of the plunger is preferably integrally molded into the plunger structure. The outer barrel has a cylindrical, hollow tubular shape to permit the inner plunger to move slidably within the outer barrel. The outer barrel is formed from a barrel base and a barrel cap. Each of the barrel base and barrel cap has a cylindrical side wall. The barrel base has a closed end and an open end. The barrel cap has an open end and an aperture at the other end of the hollow cylinder. The barrel cap and base have inner and outer diameters which permit the open end of one of the base or cap to be placed over the open end of the other and placed in a fixed position to form the barrel. The barrel cap has a jaw extending radially from the barrel cap and positioned on the cylindrical side wall close to the aperture of the barrel cap. When the barrel cap is placed in its fixed position with respect to the barrel base, the jaws of the barrel and plunger are parallel to each other.

The barrel cap has a slotted opening in the cylindrical wall extending longitudinally axially from the open end of the cap to a point in proximity to the jaw of the barrel cap. The barrel base also has a longitudinal axial slotted opening in its cylindrical wall extending from its open end to a point in proximity to its closed end.

The inner plunger also has a cylindrical, hollow shape. The interengagement of the plunger and barrel, and the telescoping action of the barrel and plunger, form an interior cylindrical channel, the length of which is compressed and extended as the barrel and plunger move axially with respect to each other. The plunger has a generally cylindrical side wall, an elongated hollow passage open at one end, and closed at the opposite and outside end, and a plunger jaw fixed at or near to the open end of the passage of the plunger. The jaw radiates outwardly from the cylindrical plunger. The outer barrel can have a guide member disposed on the interior of the elongated hollow passage, and the interior telescoping plunger will then have a guide member disposed on the exterior of its cylindrical wall and positioned so that it engages the guide member on the barrel during the telescoping movement of the barrel and plunger. Each of the barrel and the plunger has an end cap enclosing the outside end of the barrel and plunger. The term "outside end" refers to that end of the components of the assembled clip which is available for application of compression by the operator to move the barrel and plunger jaws apart. There is a slotted opening in the barrel which is positioned longitudinally on the barrel between the end cap and the jaw. The slotted opening is sufficiently narrow or otherwise restricted that the plunger cannot be inserted laterally through the slot into the interior of the barrel. A coil spring is positioned inside the interior cylindrical channel and is held therein by the end caps on the barrel and plunger.

This invention also relates to a method for assembling a parallel jaw clip comprising a) forming a hollow barrel base having a closed end and an opposite open end, a hollow barrel cap, and an inner hollow plunger with a closed end and an opposite open end, b) placing a spring within the hollow barrel base so that one end of the spring is positioned against the interior of the closed end of the barrel base, c) placing the inner plunger within the hollow barrel base so that the spring extends into said hollow inner plunger and contacts the interior of the closed end of said plunger, d) placing the hollow barrel cap over the inner plunger and over the open end of said hollow barrel base, and e) fastening said barrel cap to said barrel base to form a barrel, thereby enclosing said inner plunger and spring within said barrel.

In a more specific embodiment, the invention comprises a method of producing a parallel jaw clip comprising:

a) forming a barrel base having a cylindrical wall enclosing a hollow interior, said base having an outer diameter and an inner diameter, an open end at one end of the cylindrical wall and a closed end at the opposite end of said cylindrical wall, a base slotted opening in said cylindrical wall extending longitudinally axially from said open end to a point in proximity to its closed end, and at least one interlock on said cylindrical wall, b) forming a barrel cap having a cap cylindrical wall enclosing a cap hollow interior, said cap having an outer diameter and an inner diameter, said cap having an open end at one end of the cap cylindrical wall and an aperture at the opposite end of said cap cylindrical wall, a barrel jaw extending radially from said cap cylindrical wall and in proximity to said aperture in said barrel cap, and a cap slotted opening extending longitudinally axially from said cap open end to a point in proximity to said barrel jaw, and at least one interlock on said cap cylindrical wall positioned to engage the interlock on the base cylindrical wall when the base and cap are joined together, c) forming an inner plunger having a cylindrical side wall enclosing a plunger hollow interior, a plunger open end at one end of said plunger and a plunger closed end at the opposite end of said plunger, and a plunger jaw extending radially from said plunger cylindrical wall in proximity to said plunger open end, d) placing a spring having two extremities within the base hollow interior, so that one of the extremities is in contact with the interior of said base closed end, e) placing said inner plunger within said base hollow interior so that said spring extends into said plunger hollow interior and the opposite extremity of said spring contacts the interior of said closed end of said plunger, and so that said plunger jaw engages said base slotted opening and is movable longitudinally within said base slotted opening, f) placing the hollow interior of said barrel cap over the plunger cylindrical wall so that said plunger jaw engages said cap slotted opening and is movable longitudinally within said cap slotted opening, g) moving said barrel cap toward said barrel base so that said cap hollow interior encloses said base cylindrical wall and so that said base interlock engages said cap interlock, and so that said base slotted opening and said cap slotted opening are aligned with each other to form a barrel slotted opening, and h) positioning said plunger closed end so that it remains outside said aperture on said barrel cap.

DESCRIPTION OF THE DRAWINGS

FIG. 7 is an axial cross section view illustrating the clip in a closed state;

DESCRIPTION OF PREFERRED EMBODIMENTS AND BEST MODE OF THE INVENTION

Figure 1:
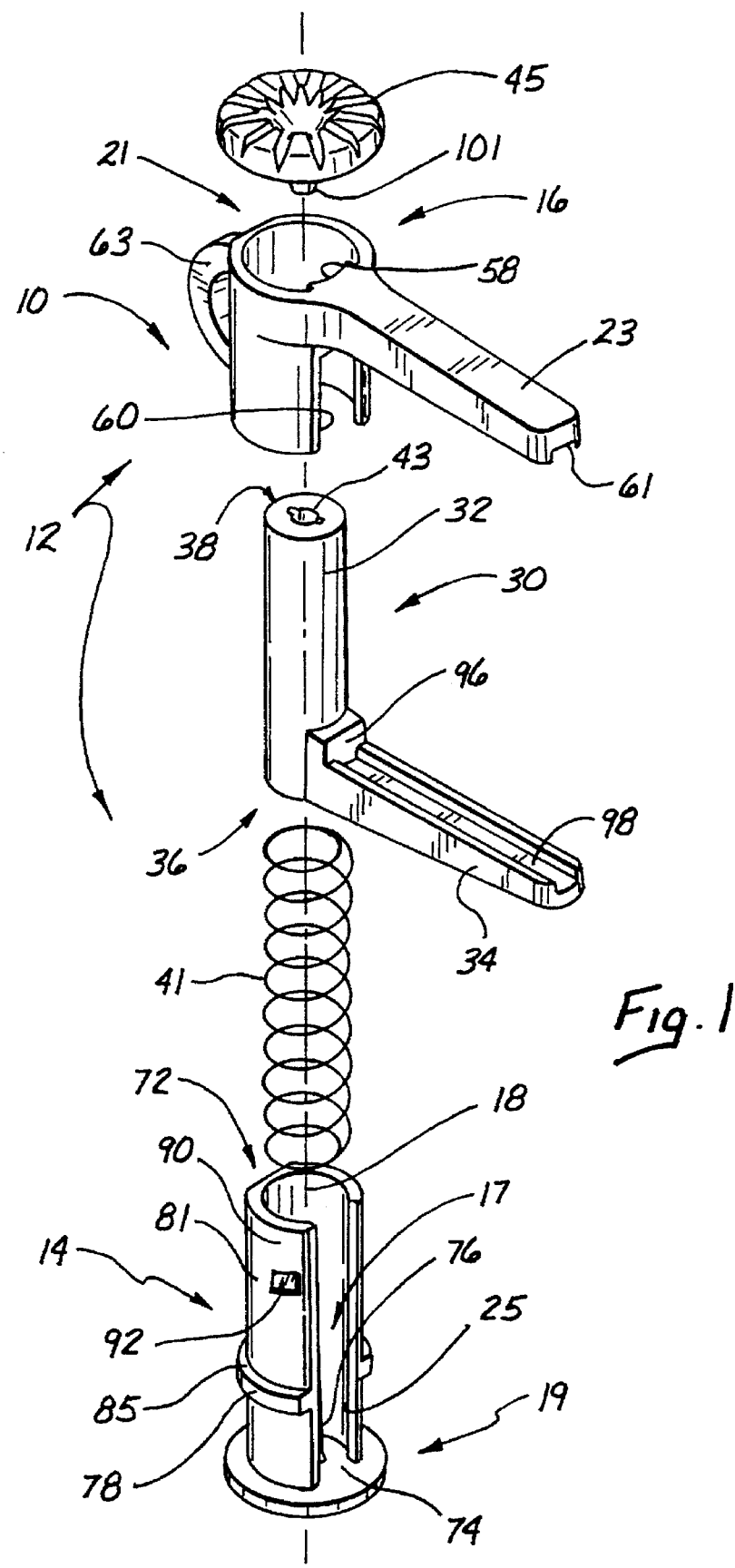
FIG. 1 is an exploded perspective view of one embodiment of the clip of the present invention, showing a barrel cap, a barrel base and other component parts in axial positions from which the components are assembled.

A surgical clip is illustrated in the exploded view of FIG. 1 and designated generally by the reference numeral 10. The clip 10 includes a barrel 12 which in this case is formed from a barrel base 14 and a barrel cap 16. The barrel 12 is generally cylindrical in configuration and includes a hollow interior region 17 extending along an axis 18 between a closed end 19 and an open end 21.

In the illustrated embodiment, the closed end 19 of the barrel 12 is formed in the barrel base 14 while the open end 21 of the barrel 12 is formed in the barrel cap 16. The barrel base 14 is also provided with a longitudinal channel 25 which extends along its length. In this embodiment, the barrel cap 16 is integral with an elongate jaw 23 which extends generally perpendicular to the axis 18. A plunger 30 is disposed within the hollow interior region 17 of the barrel 12, and is moveable along the axis 18 through the open end 21 of the barrel cap 16.

The plunger 30 includes a piston 32 and a jaw 34 extending generally perpendicular to the piston 32. In the illustrated embodiment, the piston 32 is disposed within the hollow interior region 17 and is movable along the axis 18. With the piston 32 thus disposed, the jaw 34 rides within the channel 25 in an opposing relationship to the jaw 23 of the barrel cap 16. Thus the plunger 30 is movable between a first position wherein the jaws 23 and 34 are closed, and a second position wherein the jaws 23 and 34 are open. The piston 32 also has a generally hollow configuration with a generally open end 36 and a generally closed end 38.

The plunger 30 is biased to the first position by a compression spring 41 which is disposed between the closed end 19 of the barrel base 14, and the closed end 38 of the piston 32. When the plunger 30 is in the first position, and the jaws 23 and 34 are closed, a portion of the piston 32 extends through the open end 21 of the barrel cap 16 and axially outwardly of the barrel 12. The closed end 38 of the piston 32 is provided with a hole 43 suitable sized to receive an end cap 45. In operation, a force acting on the end cap 45 relative to the closed end 19 of the barrel base 14 operates to depress the plunger 30 within the interior region 17 thereby moving the movable jaw 34 associated with the plunger 30 away from the fixed jaw 23 associated with the barrel cap 16. Release of this compressive force enables the spring 41 to return the movable jaw 34 into proximity with the fixed jaw 23.

Figure 2:
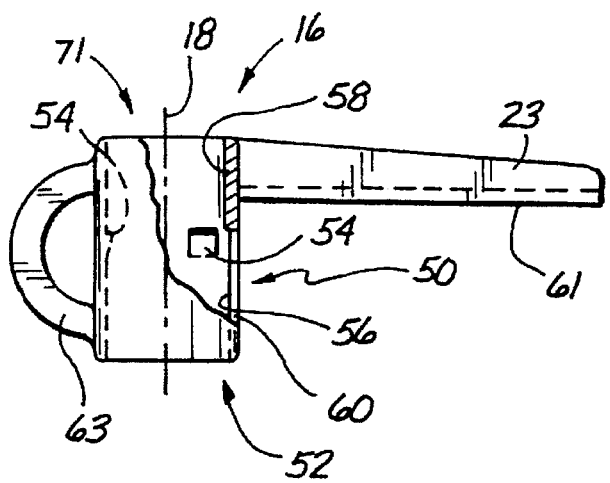
FIG. 2 is a side view partially in section of the barrel cap illustrated in FIG. 1.
Figure 3:
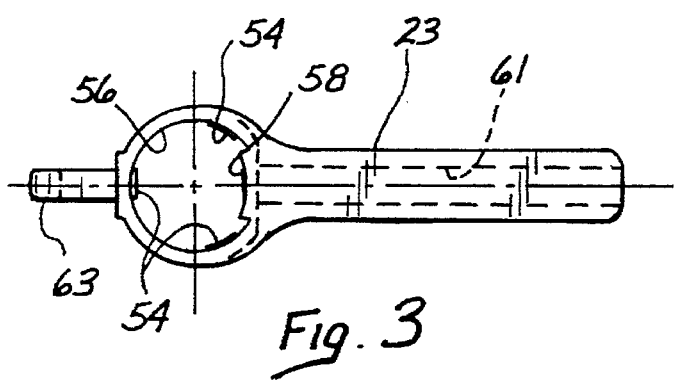
FIG. 3 is a top plan view of the barrel cap.

The barrel cap 16 is illustrated in greater detail in the side elevation view and the top view of FIGS. 2 and 3, respectively. In these views it can be seen that the barrel cap 16 includes a cylindrical portion 50 which is open not only at the open end 21, but also at the opposing end 52. A longitudinal opening 60 is formed in the wall of the cylindrical portion 50 beneath the flange 58.

A plurality of ramped shoulders 54, three in number and equally angularly spaced in the preferred embodiment, are formed on an inner surface 56 of the cylindrical portion 50. A flange 58 also extends inwardly of the inner surface 56 in proximity to the open end 21. In a preferred embodiment, the fixed jaw 23 extends transversly to the axis 18 and outwardly of the cylindrical portion 50 in proximity to the flange 58 and the open end 21. This jaw 23 can be provided with a longitudinal channel 61 to facilitate the insertion of an insert onto the jaw 23. Finally, a handle 63 can be provided on the barrel cap 16 to facilitate placement and manipulation of the clip 10.

Figure 4:
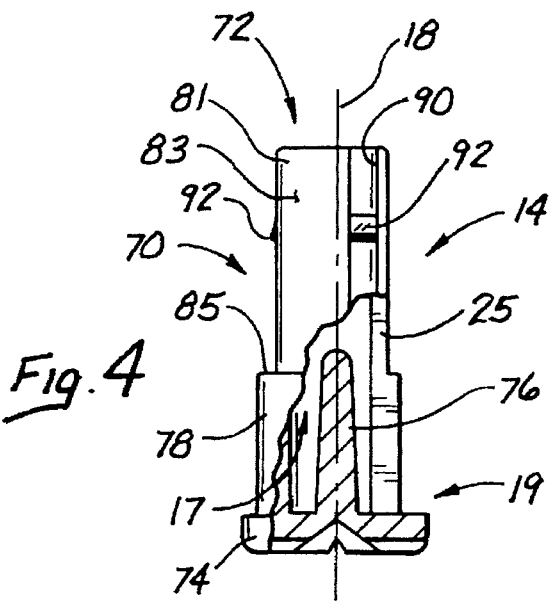
FIG. 4 is a side elevation view, partially in section of the barrel base illustrated in FIG. 1.
Figure 5:
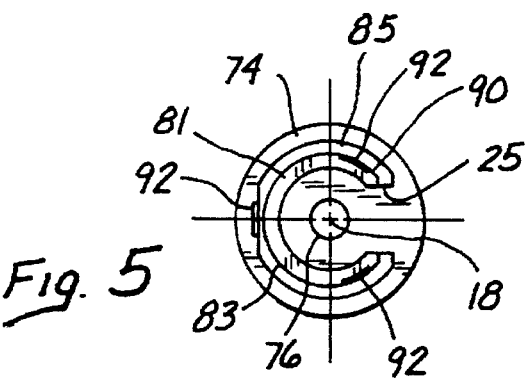
FIG. 5 is a top plan view of the barrel base illustrated in FIG. 4.

The barrel cap 16 is sized and configured to facilitate a telescoping, snap fit relationship with the barrel base 14. Together, the cap 16 and base 14 form the barrel 12 as previously mentioned. The barrel base 14 is illustrated in greater detail in the side elevation view and top view of FIGS. 4 and 5 respectively. The base 14 also has the general configuration of a cylinder 70 extending between the closed end 19 and an open end 72. In the preferred embodiment, the end 19 is closed by an end cap 74. A post 76 is disposed to extend from the end cap 74 within the interior region 17 and along the axis 18. This post 76 functions to facilitate axial alignment of the spring 41 (FIG. 1) within the interior region 17.

The cylinder 70 in the preferred embodiment includes an enlarged section 78 near the closed end 19 and a narrow section 81 near the open end 72. An outer surface 83 of the narrow section 81 extends to a shoulder 85 where the narrow section 81 engages the enlarged section 78.

A slot 90 is recessed from the surface 83 and extends longitudinally of the narrow section 81. A ramped shoulder 92 is formed along the slot 90 and facilitates a snap fit relationship with the ramped shoulder 54 of the cap 16 in a manner described in greater detail below. A slot 90 and associated ramped shoulder 92 is provided for each of the shoulders 54 of the cap 16.

Figure 6:
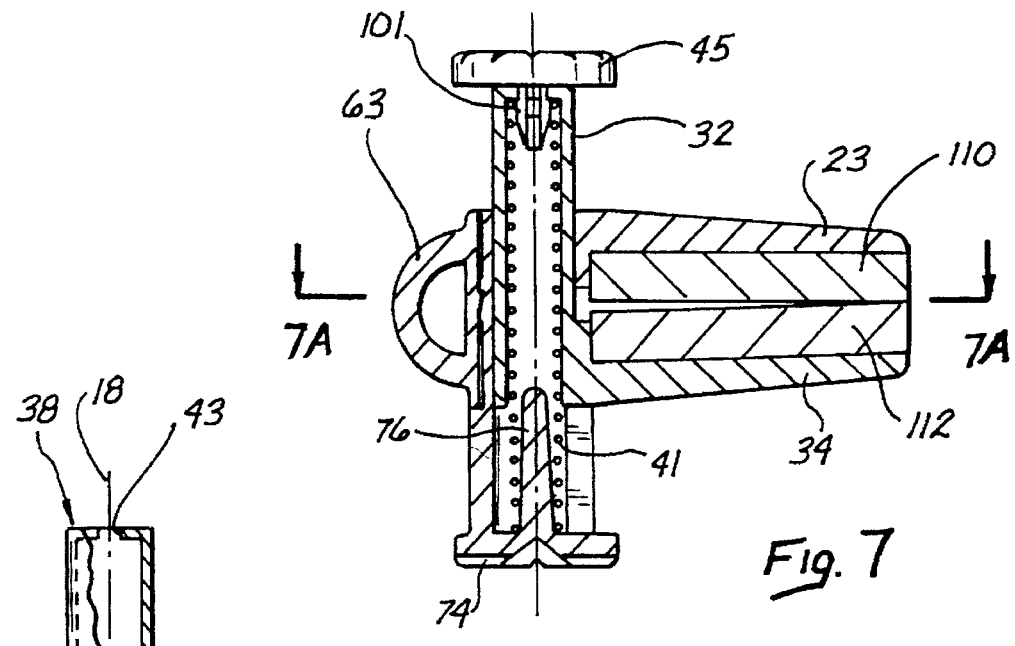
FIG. 6 is a side elevation view partially in section of a plunger associated with the present invention.
Figure 6:
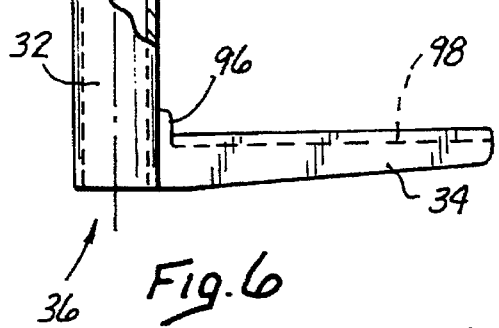

The plunger 30 is illustrated in greater detail in the side elevation view of FIG. 6. In this view it can be seen that the piston 32 of the plunger 30 extends between the closed end 38 and the open end 36. The movable jaw 34, which has a fixed relationship with the piston 32 extends generally transverse to the axis 18 near the open end 36. A flange 96, best illustrated in FIG. 1, extends between the piston 32 and the jaw 34 in order to facilitate alignment of the plunger 30 with respect to the base 14. In a preferred embodiment, the jaw 34 is also provided with a longitudinal channel 98 similar to the channel 61 of the jaw 23. A variety of soft jaw or fiber inserts can be mounted in these channels 61, 98.

Assembly of the clip 10, which is of particular advantage in the present invention, is best understood with further reference to FIG. 1. Initially, the base 14 can be supported on the end cap 74 with the axis 18 extending generally perpendicular to the supporting surface. The spring 41 can then be axially loaded into the hollow interior region 17 of the base 14. This is accomplished in a preferred method by dropping the spring 41 through the open end 72 and along the axis 18 into the region 17 where the spring 41 is supported at one end on the end cap 74 and around the post 76.

At this point, the plunger 30 can also be added to the assembly. In a preferred method, the piston 32 is merely moved along the axis 18 where its open end 36 extends over the spring 41 within the interior region 17. The flange 96 rides along the channel 25 of the base 14 and seeks to maintain the movable jaw 34 in a preferred radial orientation with respect to the base 14.

With the spring 41 and piston 32 appropriately disposed within the interior region 17, the barrel cap 16 can now be added to the assembly. Again it is particularly desirable that the cap 16 can be moved axially over the piston 32 and onto the narrow section 81 of the cylinder 70.

As the barrel cap 16 extends in a telescoping relationship over the barrel base 14, the ramped shoulders 54 ride in the slots 90 to facilitate alignment of the fixed jaw 23 relative to the movable jaw 34. This alignment is further enhanced by the flange 96 which rides along the opening 60 in the cap 16. When the ramped shoulders 54 of the cap 16 engage the ramped shoulders 92 of the base 14, further axial pressure will cause each associated pair of shoulders 54 and 92 to engage in a fixed detent relationship. The resulting fixed relationship between the base 14 and the cap 16 is facilitated by the juxtaposed relationship between the cap 16 and the shoulder 85 of the base 14. Thus the cap 16 is held in a fixed relationship with the base 14 where further downward movement of the cap 16 is inhibited by the shoulder 85 and further upward movement of the cap 16 is inhibited by the interlocking relationship of the shoulders 54 and 92.

With the barrel formed by the axial snap fit relationship between the cap 16 and base 14, the closed end 38 of the piston 32 will extend through the open end 21 of the barrel cap 16. At this point, a projection 101 associated with the end cap 45 can be inserted into the hole 43 on the closed end 38 of the plunger 30. It will be noted that even this final snap fit relationship between the piston 32 and the end cap 45 is accomplished with an axial force.

It can now be appreciated that the entire assembly of the clip 10 is accomplished by loading the various elements along the axis 18 and then applying snap fit forces along the same axis 18. The resulting construction of the clip greatly enhances the ease of assembly thereby significantly reducing the cost of the manufacture. The clips can be easily formed in a multiple jig (not shown) where an ultimate axial force can be applied to several of the clips simultaneously in order to achieve the snap fit assembly for each clip 10.

Figure 7A:
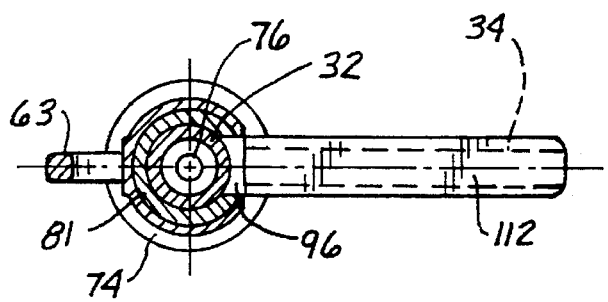
FIG. 7a is a cross section view of the clip taken along lines 7a—7a of FIG. 7.
Figure 8:
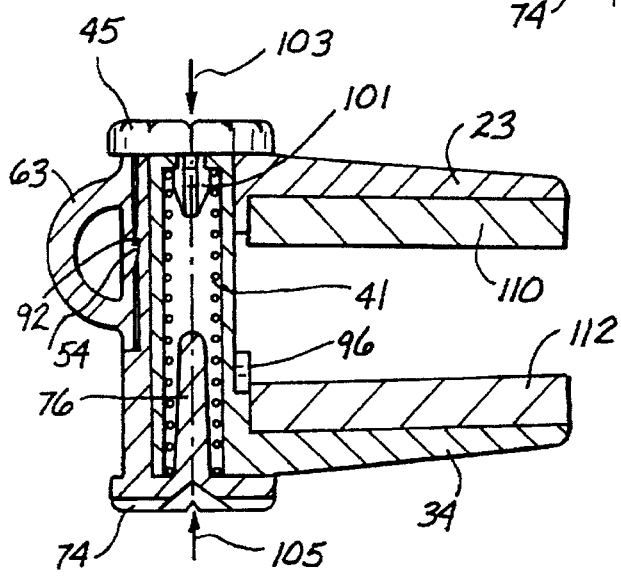
FIG. 8 is an axial cross section view illustrating the clip in an open state.

Operation of the clip 10 can be best understood with reference to FIG. 7 and 8. In FIG. 7, the clip 10 is illustrated in its first state wherein the jaws 23 and 34 are automatically biased into close proximity. Under the pressure of the compression spring 41, the closed end 19 of the base 14 and 38 of the piston 32 are separated the maximum distance. Since the jaw 23 has a fixed relationship with the base 14 and since the jaw 34 is integral with the plunger 30, this separation of the closed ends 19 and 38 results in the close proximal relationship between the jaws 23 and 34.

To open the clip 10, a compression force can be applied as illustrated in FIG. 8 by arrows 103 and 105. Forces acting along these arrows 103, 105 will typically be provided between a user's finger and thumb which will engage the end caps 45 and 74. The compression force represented by the arrows 103, 105 acts to move the piston 32 further into the interior region 17 against the bias of the spring 41. This movement of the plunger 30 relative to the base 14 also moves the movable jaw 34 relative to to the fixed jaw 23. Thus, by axially compressing the end caps 45, 74, the jaws 23, 34 separate to an open state as illustrated in FIG. 8. In FIGS. 7 and 8, inserts 110 and 112 are illustrated securely mounted in the channels 61 and 98 of the jaw 23 and 34, respectively.

By applying the compressive force illustrated by the arrows 103, 105 and opening the jaws 23 and 34, the clip 10 can be applied to a body conduit, (not shown) such as a vessel. With the vessel disposed between the jaws 23, 34, the compressive force can be removed thereby permitting the spring 41 to bias the jaws 23, 34 toward each other. This bias will in turn create a compressive force on the conduit to occlude the conduit. This occlusion occurs automatically as the clip 10 is biased to the closed position illustrated in FIG. 7. The clip 10 can be removed from the conduit by again applying the compressive force along arrows 103 and 105 to open the jaws 23, Although the invention has been disclosed with reference to preferred embodiments and method steps, it will be apparent that the clip 10 can be otherwise embodied and manufactured. Accordingly, the concept should not be limited to the specific embodiments and method steps disclosed, but rather determined only with reference to the following claims.

What is claimed is:

1. A parallel jaw base clip comprising:
   an outer barrel having first and second ends and including
      a barrel base having a first end, a second end, and a hollow interior, the first end of the base defining the first end of the barrel, and the second end of the base including a base stop surface, and
      a barrel cap having a first open end, a second open end, and a hollow interior, the first open end engaging the second end of the barrel base, and the second open end defining the second end of the barrel;
   a hollow inner plunger slidably received in the hollow interior of the barrel base, the plunger having a base end positioned in the barrel base and a cap end opposite the base end; and
   a spring positioned within the hollow interiors of the barrel and the plunger, the spring having a tint end in contact with the base stop surface and a second end in contact with the cap end of the plunger, the spring biasing the plunger to an extended position wherein the cap end of the plunger projects through the second open end of the barrel cap.

2. A parallel jaw clip according to claim 1 wherein said cap end of the plunger is integrally formed with the inner plunger.

3. A parallel jaw clip according to claim 1 wherein said plunger cap end is attached to a plunger end cap which has a larger diameter than the diameter of the barrel cap hollow interior.

4. A parallel jaw clip according to claim 1, wherein:
   the barrel base includes a cylindrical wall defining a first outer diameter;
   the barrel cap includes a cylindrical wall defining a second outer diameter; and
   the second outer diameter is larger than the first outer diameter, thereby permitting the cylindrical wall of the barrel cap to fit over the cylindrical wall of the barrel base to form the outer barrel.

5. A parallel jaw clip according to claim 4 wherein said barrel base has a barrel cap stop positioned on said cylindrical wall.

6. A parallel jaw clip according to claim 1 wherein a barrel jaw attached to said barrel, and a plunger jaw attached to said plunger each have a recess extending at least part of the length of said jaws, wherein said recesses face each other, and wherein each of said recesses holds a pad.

7. A parallel jaw clip according to claim 6 wherein said plunger jaw is positioned in proximity to said base end of said plunger.

8. A parallel jaw clip according to claim 1 wherein a plunger end cap is attached to said plunger through a snap fitting.

9. A parallel jaw clip according to claim 1 wherein said barrel base and said barrel cap are joined together through a snap fitting.

10. A parallel jaw clip according to claim 1, wherein the barrel defines a longitudinal axis and wherein the barrel base includes a spring guide pin projecting from the second end of the barrel into the hollow interior of the barrel cap in vertical alignment with the longitudinal axis of the barrel.

11. A parallel jaw clip according to claim 1, wherein the first end of the barrel base is substantially closed.

12. A parallel jaw clip according to claim 11, wherein the base includes a cylindrical wall and the first end of the barrel base is integral with the cylindrical wall.

13. A parallel jaw clip according to claim 1, wherein the cap end of the inner plunger is substantially closed.

14. A parallel jaw clip according to claim 13, wherein the inner plunger includes a cylindrical wall, and the cap end of the inner plunger is integral with the cylindrical wall.

15. A parallel jaw clip comprising
   a) an outer barrel comprising
      i) a barrel base having a cylindrical wall enclosing a hollow interior, said base having an outer diameter and an inner diameter, an open end at one end of the cylindrical wall and a closed end at the opposite end of said cylindrical wall, a base slotted opening in said cylindrical wall extending longitudinally axially from said open end to a point in proximity to its closed end, and at least one interlock on said cylindrical wall, and
      ii) a barrel cap having a cylindrical wall enclosing a hollow interior, said cap having an outer diameter and an inner diameter, said cap having an open end at one end of the cap cylindrical wall and an aperture at the opposite end of said cap cylindrical wall, a barrel jaw extending radially from said cap cylindrical wall, and a cap slotted opening extending longitudinally axially from said cap open end engaging the base cylindrical wall to a point in proximity to the barrel jaw, and at least one interlock on said cap cylindrical wall positioned to engage the interlock on the base cylindrical wall when the base and cap are joined together,
      iii) the base and cap slotted openings being aligned so that the slotted openings overlap each other when said base and cap are joined together, thereby forming a barrel slotted opening, and
      iv) the inner and outer diameters of said base and cap being of such dimensions that one of the base or cap fits within the hollow interior of the other cap or base, thereby forming a barrel hollow interior;
   b) an inner plunger having a cylindrical wall enclosing a plunger hollow interior, said plunger having an outer diameter and an inner diameter, said plunger having an open end at one end of the plunger cylindrical wall and a closed end at the opposite end of said plunger cylindrical wall, and a plunger jaw extending radially from said plunger cylindrical wall at or near said plunger open end, said plunger being slidably positioned within said barrel hollow interior so that said plunger jaw extends through said barrel slotted opening and said plunger can move longitudinally axially through said barrel hollow interior, and said plunger jaw can move longitudinally axially through said barrel slotted opening; and
   c) a spring having two extremities and positioned within said plunger hollow interior and said barrel hollow interior, one of said spring extremities being in proximity to said barrel base closed end and the second extremity being in proximity to said plunger closed end, said spring being under relatively low compression when said plunger jaw is in proximity to said barrel jaw and under relatively high compression when said plunger jaw is removed from proximity to said barrel jaw.

16. A parallel jaw clip according to claim 15 wherein said outer barrel has a handle on its cylindrical wall at a point circumferentially displaced from said barrel jaw.

17. A parallel jaw clip according to claim 16, wherein the spring biases the plunger to an extended position wherein the closed end of the plunger projects through the aperture in the cap cylindrical wall.

18. A parallel jaw clip according to claim 15, wherein the barrel cap and the barrel base are formed of sufficiently rigid material and the slotted openings in the barrel cap and the barrel base are sufficiently restricted to prevent lateral insertion of the plunger through the slotted openings.

19. A method for assembling a surgical clip comprising
   a) forming a hollow barrel base having a closed end and an opposing open end, a hollow barrel cap, and a hollow plunger having a closed end and an opposing open end,
   b) placing a spring within the hollow barrel base so that one end of the spring is positioned against the closed end of the barrel base,
   c) inserting the inner plunger axially into the hollow barrel base so that the spring extends into said hollow plunger and contacts the closed end of said plunger,
   d) placing the hollow barrel cap over the inner plunger and over the open end of said hollow barrel base, and
   e) fastening said barrel cap to said barrel base to form a barrel, thereby enclosing said inner plunger and spring within said barrel.

20. A method according to claim 19 wherein the outer diameter of said barrel cap is smaller than the inner diameter of said barrel base, thereby permitting said barrel base hollow interior to enclose the outer cylindrical wall of said barrel cap.

21. A method according to claim 19, wherein the step of fastening said barrel cap to said barrel base comprises the step of snap-fitting said barrel cap to said barrel base.

22. A method for assembling a surgical clip comprising
   a) forming a barrel base having a cylindrical wall enclosing a hollow interior, said base having an outer diameter and an inner diameter, an open end at one end of the cylindrical wall and a closed end at the opposite end of said cylindrical wall, a base slotted opening in said cylindrical wall extending longitudinally axially from said open end to a point in proximity to its closed end, and at least one interlock on said cylindrical wall,
   b) forming a barrel cap having a cap cylindrical wall enclosing a cap hollow interior, said cap having an outer diameter and an inner diameter, said cap having an open end at one end of the cap cylindrical wall and an aperture at the opposite end of said cap cylindrical wall, a barrel jaw extending radially from said cap cylindrical wall and in proximity to said aperture in said barrel cap, and a cap slotted opening extending longitudinally axially from said cap open end to a point in proximity to said barrel jaw, and at least one interlock on said cap cylindrical wall positioned to engage the interlock on the base cylindrical wall when the base and cap are joined together,
   c) forming an inner plunger having a cylindrical side wall enclosing a plunger hollow interior, a plunger open end at one end of said plunger and a plunger closed end at the opposite end of said plunger, and a plunger jaw extending radially from said plunger cylindrical wall in proximity to said plunger open end,
   d) placing a spring having two extremities within the base hollow interior, so that one of the extremities is in contact with the interior of said base closed end,
   e) inserting said inner plunger axially into said base hollow interior so that said spring extends into said plunger hollow interior and the opposite extremity of said spring contacts the interior of said closed end of said plunger, and so that said plunger jaw engages said base slotted opening and is movable longitudinally within said base slotted opening,
   f) placing the hollow interior of said barrel cap over the plunger cylindrical wall so that said plunger jaw engages said cap slotted opening and is movable longitudinally within said cap slotted opening,
   g) moving said barrel cap toward said barrel base so that said cap hollow interior encloses said base cylindrical wall and so that said base interlock engages said cap interlock, and so that said base slotted opening and said cap slotted opening are aligned with each other to form a barrel slotted opening, and
   h) positioning said plunger closed end so that it remains outside said aperture on said barrel cap.

23. A method according to claim 22 wherein said positioning of said plunger closed end is accomplished by attaching a plunger end cap to said plunger closed end wherein said plunger end cap has a diameter greater than the diameter of said aperture.

24. A method according to claim 22 wherein said jaws on said barrel and said plunger are aligned in parallel relationship to each other with the jaw on the plunger positioned closer to the outside end of the barrel base than the barrel jaw, and with the object-engaging faces of said jaws facing each other, so that the jaw on said plunger is movable within said barrel slotted opening when the plunger is moved slidably back and forth with respect to said barrel.

* * * * *